US008740868B2

(12) United States Patent
Chambers

(10) Patent No.: US 8,740,868 B2
(45) Date of Patent: Jun. 3, 2014

(54) MALE UNDERGARMENT DISCHARGE SHIELD

(76) Inventor: Anthony Chambers, Port Saint Lucie, FL (US)

( * ) Notice: Subject to any disclaimer, the term of this patent is extended or adjusted under 35 U.S.C. 154(b) by 0 days.

(21) Appl. No.: 13/210,467

(22) Filed: Aug. 16, 2011

(65) Prior Publication Data

US 2013/0046258 A1    Feb. 21, 2013

(51) Int. Cl.
*A61F 5/44* (2006.01)
(52) U.S. Cl.
USPC .......................................................... 604/349
(58) Field of Classification Search
USPC .......................................................... 604/349
See application file for complete search history.

(56) References Cited

U.S. PATENT DOCUMENTS

| | | | | |
|---|---|---|---|---|
| 3,314,422 A | * | 4/1967 | Phillips | 128/846 |
| 3,517,666 A | * | 6/1970 | Atlee | 602/68 |
| 4,155,360 A | * | 5/1979 | Erickson | 128/891 |
| 4,576,599 A | | 3/1986 | Lipner | |
| 4,675,012 A | * | 6/1987 | Rooyakkers | 604/349 |
| 4,863,448 A | | 9/1989 | Berg | |
| 5,330,822 A | * | 7/1994 | Berg et al. | 428/192 |
| 5,397,626 A | * | 3/1995 | Berg et al. | 442/393 |
| 5,476,459 A | * | 12/1995 | Yang | 604/385.26 |
| 5,486,168 A | | 1/1996 | Runeman | |
| 5,556,393 A | * | 9/1996 | R onnberg | 604/385.26 |
| 5,558,659 A | * | 9/1996 | Sherrod et al. | 604/385.26 |
| 5,651,778 A | * | 7/1997 | Melius et al. | 604/385.19 |
| 5,702,381 A | * | 12/1997 | Cottenden | 604/385.01 |
| 5,716,350 A | * | 2/1998 | Ryan | 604/385.09 |
| 6,013,066 A | | 1/2000 | Samuelsson | |
| 6,132,412 A | * | 10/2000 | Jones | 604/400 |
| 6,245,036 B1 | * | 6/2001 | McRoberts et al. | 602/67 |
| 6,409,712 B1 | | 6/2002 | Dutari | |
| 6,440,112 B1 | * | 8/2002 | Glaug et al. | 604/385.01 |
| 6,447,493 B1 | | 9/2002 | Simpson | |
| 6,692,603 B1 | * | 2/2004 | Lindsay et al. | 156/209 |
| 6,984,279 B2 | | 1/2006 | Mortell | |
| 7,195,619 B2 | | 3/2007 | Manasek | |
| 7,341,580 B2 | | 3/2008 | Hamilton-Vance | |
| 8,142,408 B2 | * | 3/2012 | Reddy | 604/385.09 |
| 2003/0125690 A1 | * | 7/2003 | Hermansson et al. | 604/385.01 |
| 2004/0059308 A1 | | 3/2004 | Odderson | |
| 2004/0097893 A1 | | 5/2004 | Elfstrom | |
| 2004/0111073 A1 | * | 6/2004 | Hermansson et al. | 604/349 |
| 2005/0032952 A1 | * | 2/2005 | Bonfanti et al. | 524/306 |
| 2007/0163030 A1 | * | 7/2007 | Reddy | 2/403 |
| 2007/0255248 A1 | * | 11/2007 | Hendren et al. | 604/395 |
| 2008/0082072 A1 | * | 4/2008 | Helmfridsson et al. | 604/385.19 |
| 2009/0062765 A1 | * | 3/2009 | Schermerhorn et al. | 604/393 |
| 2009/0255539 A1 | * | 10/2009 | Reddy | 128/846 |

* cited by examiner

*Primary Examiner* — Susan Su
*Assistant Examiner* — Guy K Townsend
(74) *Attorney, Agent, or Firm* — Daniel Boudwin; Global Intellectual Property Agency LLC

(57) ABSTRACT

A male fluid discharge guard and collection device for use in connection with a male undergarment. The device comprises a cup-shaped pocket with a backside and a forward lip, the backside being attachable to a pair of male undergarments using an adhesive bonding strip, while the forward lip is extendable and retractable to provide an opening for which fluid may be discharged into the device. The pad provides a shield that prevents a male undergarment from being saturated or otherwise soiled by discharge from a male genitalia. The device may be utilized with undergarment briefs, boxers or boxer briefs using the same retention means and mode of operation.

3 Claims, 1 Drawing Sheet

MALE UNDERGARMENT DISCHARGE SHIELD

BACKGROUND OF THE INVENTION

1. Field of the Invention

The present invention relates to undergarment pads and shields for fluid discharge collection. More specifically, the present invention relates to a male undergarment pad for collection and absorption of fluid discharge from male genitalia to prevent contents from contacting and soiling the undergarment.

2. Description of the Prior Art

Post urinary drip, ejaculate or incontinence can result in fluid secretion from a male penis. This fluid can stain, soil or adhere to the garments of an affected individual, which can be embarrassing, troublesome and stain clothing. Undergarment pads are commonly used to absorb body fluids that may leak or discharge while an individual is wearing clothes. Typical pads have applications for female users for absorbing fluid from the vagina during a menstrual cycle; however few pads or guards are available for males to address the problem of incontinence or fluid discharge from a penis.

In addition to sanitary napkins, panty liners and absorbent pads for women, some individuals use incontinence pads and diapers to absorb urine where the individual is not able to control their bladder or bowels. These devices can be bulky, fluffy and have an obvious visual signature while being worn. They are not adapted for use in everyday situations, or in situations wherein the user prefers to conceal its presence. Further development of undergarment pads is necessary for the specific needs of a male. It would be advantageous to have a pad insert that is available to absorb urine or semen that may occasionally discharge in small amounts from male genitalia. Such body fluids stain the individual's undergarments and thus it would be preferable to insert a guard or pad to protect the undergarments from such fluids.

The present invention provides a guard that is adapted to receive ejected or secreted fluid from a penis, and one that is wearable in conjunction with a normal pair of undergarments and in any situation. The pad comprises a backing surface with an adhesive or similar attachment means for securing the device to the inner surface of an undergarment. A forward lip is provided to form a conical shaped cup with a lower forward lip than the backing surface. The forward lip can be pulled forward from the backing surface to reveal an inner volume for which to collect fluid and retain the same. The inner volume may optionally be coated or supplied with a gel that absorbs and retains the fluid, preventing leaks or spillage. The walls of the pad are impermeable to liquid, preventing seepage, saturation or leaking of fluid.

Several devices have been disclosed in the prior art that provide a sanitary pad or guard for use with a male undergarment or to provide novelty with regard to absorbing male genitalia discharge. These devices have several drawbacks to their construction that are resolved by the present invention, most notably the size, structure and versatility of the device and its usefulness for all individuals with fluid discharge or incontinence.

U.S. Pat. No. 4,863,448 to Berg is one such device that describes a post urination drip collector that forms a cap that is adapted to mate with the exterior of the glans penis. In its working position, the drip collector is mated using adhesive. In its stowed position, the device may be rolled into a substantially flat circle and packaged in foil or plastic. The Berg device describes one that acts directly on the male genitalia, as opposed to a device that is attachable to the undergarment of a user for the collection of fluid.

U.S. Pat. No. 7,195,619 to Manasek is a device that describes an anal region undergarment liner for use by male and female anatomy. The device comprises an impervious outer layer, an absorbent middle layer and a liquid-permeable bodymost layer. The device is attachable to an undergarment of a user and absorbs anal leakage therefrom. This device is suited for anal leakage, as opposed to male genitalia discharge. Its structure and intent differ from the present invention, and therefore is unsuited for the task of collecting and containing male genitalia discharge.

U.S. Pat. No. 6,013,066 to Samuelsson describes an absorbent article adapted for use in conjunction with an undergarment for absorbing fluid from users with mild incontinence. The device describes an elongated pad, mounted in the crotch region of an undergarment, comprising an outward facing liquid impermeable layer and an inward facing permeable layer. Two flaps provide a means to secure the device to the undergarment of a wearer. The structure of the Samuelsson patent is one of an elongated pad with several layers for absorbing liquid. While this device may be suited for small amount of fluid, it does not supply adequate capacity and enclosure for larger amounts of fluid. The present invention comprises a cupped device that can accept the head of a male penis and enclose any leaking fluid. The present invention may provide an absorbent layer for retention of fluid therein.

U.S. Pat. No. 6,409,712 to Dutari describes a disposable undergarment shield comprising an elongated pad region suitable for absorbing secretions from a male genitalia and protecting the undergarments from soiling. The pads comprise an elongated body section with a midsection slit to accommodate extraction of the male genitalia for urination purposes. Similar to the Samuelsson patent, the Dutari patent describes a layered pad, as opposed to a cupped shield and collection device as described in the present invention.

U.S. Pat. No. 4,576,599 to Lipner describes a sanitary pad adapted to mount and attach to the end of a male penis. The device comprises a T-shaped construction of a layered pad of absorbent material, water barrier layer and an additional, relatively thin absorbent layer. The device is folded to form semi-cylindrical portions that envelop a wearer's penis to absorb fluid therefrom. This device is similar to the Berg patent, in which a pad is provided adapted to mount and attach to the end of a wearer's penis and absorb fluid excreted therefrom.

U.S. Pat. No. 6,447,493 to Simpson describes a thin absorbent patch adapted for mounting to the undergarment of a male user for protecting the same from leakage of bodily discharges. The patch comprises a flexible, absorbent article with a fluid-impermeable cover, fluid-impermeable deflecting baffle and an engulfing absorbent material therebetween. The device does not provide a cupped structure or one that is designed with an opening to accept fluid or the head of a penis for fluid discharge containment and absorption.

U.S. Pat. No. 7,341,580 to Hamilton-Vance describes a protective liner adapted to be placed within the garment of a wearer for the absorption of waste materials. The pad comprises a liner structure with elastic ribs and a pair of grip tabs for eliminating the need for a diaper product. Similar to the aforementioned undergarment pad patents, the Hamilton-Vance patent provides a lining of absorbent layers, attachable to an undergarment for absorption of fluid from a user. The device structure differs from the present invention, wherein an expandable cup is provided.

U.S. Published Patent Application No. 2004/0097893 to Elfstrom describes an absorbent product for men that is adapted to prevent urine from contacting the user's undergarments. The product comprises a body that tapers to a front section and a crotch section. A liquid barrier extends across the full extent of the crotch section to prevent leakage of fluid. The Elfstrom patent describes a cup-like device attached to several other sections. Its structure differs from the present invention, and does not afford the same comfort and leak protection. The present invention simply attaches directly to a user's undergarments, and involves no extra folded sections to use.

U.S. Published Patent Application No. 2004/0059308 to Odderson describes a post-void, urinary drip napkin adapted to allow a user to shake his penis without directly contacting the same. The napkin comprises an open end, a closed end, and a conical shape that can fold flat. The napkin is placed over the penis during use, and then subsequently discarded. The Odderson device does not contemplate attachment to a user's undergarments, but rather provides a sanitary napkin for absorbing and collecting urinary drip post-urination.

U.S. Pat. No. 5,486,168 to Runeman describes a male incontinence guard that includes an inner, liquid permeable layer and an outer, liquid impermeable layer. An absorbent pad is disposed between layers, while the structure of the pad tapers from its forward end to its rear termination forming a conical, convex-shaped pad. This device is bulky, cumbersome and ideally suited for those with severe incontinence. The present invention provides a remedy that can be adapted for use by all users, while providing a pad that is concealable and wearable with most any garment.

The present invention relates to a male undergarment fluid collection device. The male undergarment according to the present invention provides a means to capture body fluids and to therefore prevent male undergarments from being soiled by bodily fluids that may be discharged following an erection, post-urinary drip or due to incontinence. The undergarment pad comprises a funnel shape and an attachment means for securing the device to an undergarment of a user. It substantially diverges in design elements from the prior art and consequently it is clear that there is a need in the art for an improvement to existing undergarment pad devices. In this regard the instant invention substantially fulfills these needs.

SUMMARY OF THE INVENTION

In view of the foregoing disadvantages inherent in the known types of male undergarment fluid collection devices now present in the prior art, the present invention provides a new fluid collection device wherein the same can be utilized for providing convenience for the user when collecting and retaining fluid from a penis and attachable to an undergarment.

It is therefore an object of the present invention to provide a new and improved male undergarment fluid collection device that has all of the advantages of the prior art and none of the disadvantages.

Another object of the present invention is to provide a concealable fluid discharge collection and retainment article that is attachable to the interior surface of a wearer's undergarment for preventing leakage and soiling thereof due to penile discharge.

Another object of the present invention is to provide a cup-shaped device with a adhesive backing surface and a shelf-like frontal lip that is collapsible against the backing surface or extendable therefrom to provide an interior volume for fluid collection.

Another object of the present invention is to provide a fluid discharge collection device that is disposable after use, and one that is collapsible into a flat shape prior to deployment and use.

Yet another object of the present invention is to provide a device with a liquid impermeable shell structure and one that incorporates a gel interior volume that absorbs fluid discharge from a user's penis.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
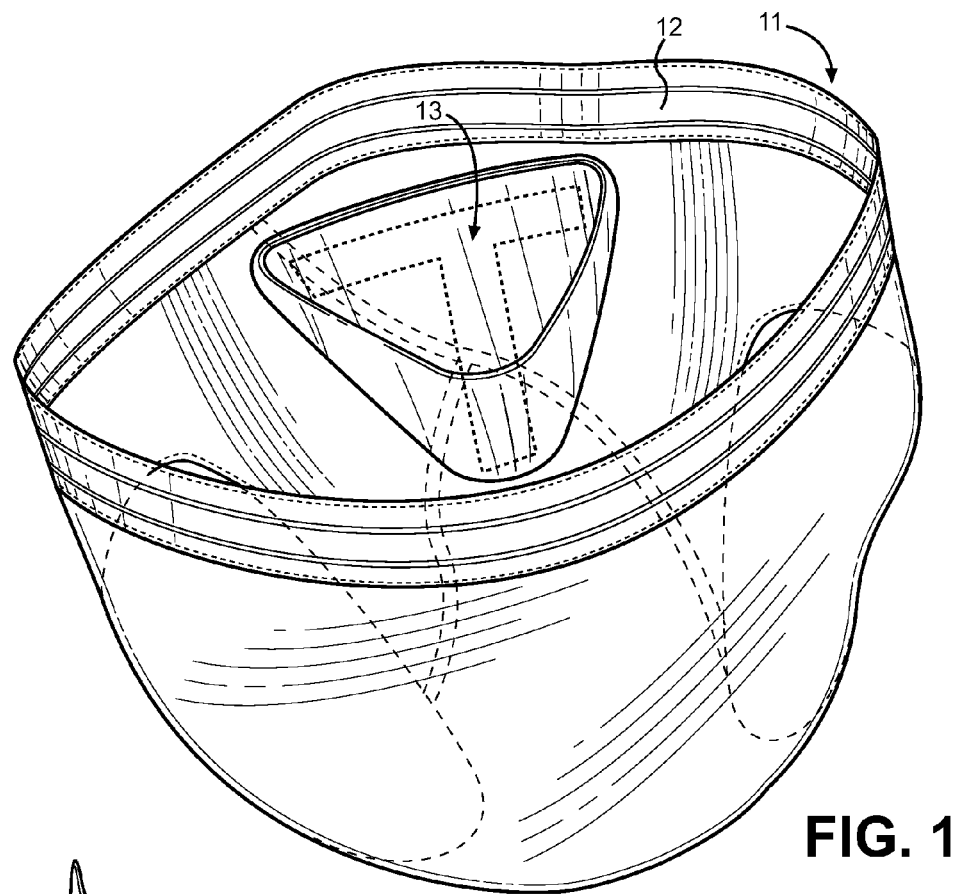
FIG. 1 shows a perspective view of the present invention in a working position, situated in the crotch region of an undergarment and adhered thereto.

Referring now to FIG. 1, there is shown a perspective view of a fluid discharge collection device 13 as described by the present invention in a working position, attached to the crotch region of a male undergarment 11. The device 13 comprises a backing surface adapted to conform to the surface of a user's undergarment 11, being boxers, boxer briefs or briefs. The backing surface provides an adhesive means for securing the device to the undergarment crotch surface below the waistline 12. In a preferred embodiment, the adhesive means comprises a T-shaped adhesive film that includes a tacky outer surface. The adhesive is covered by a removable film prior to use, then the adhesive is pressed against the undergarment to provide securement thereto. The backing surface wraps around to form a forward lip having a lower upper edge than the backing surface. The lower edge creates a cup shape and widened opening for acceptance of fluid discharge, and the penis itself during use.

Figure 2:
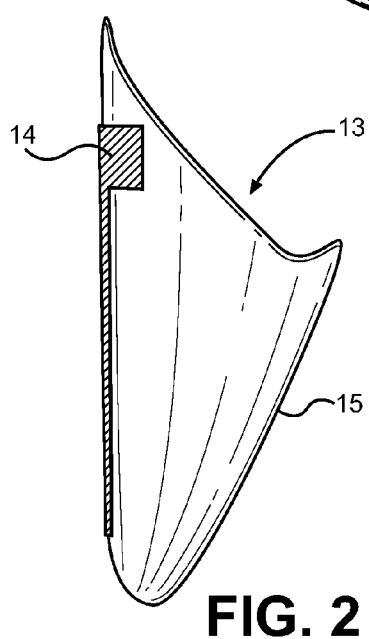
FIG. 2 shows a side view of the present invention, wherein the forward lip is extended away from the backing surface.

The forward lip can be pulled away from the backing surface to reveal an inner volume for containment of fluid therein. Referring now to FIG. 2, there is shown a view of the forward lip 15 pulled away from the backing surface 14, allowing the device to form an open cup for collection of urine, semen or other fluid discharge from a penis. The backing surface 14 and the forward lip form together to create a funnel shape, wherein the base of the device comprises a smaller cross-section than the top. The backing surface 15 converges with the forward lip 15 along the sides of the device, in which a crease is formed to allow collapsibility of the device when not in use.

Figure 3:
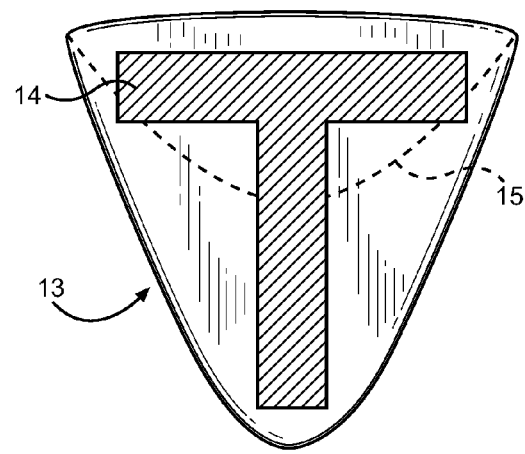
FIG. 3 shows a frontal view of the present invention, including a T-shaped adhesive bonding strip for attachment of the device to a user's undergarment.

Referring now to FIG. 3, there is shown a frontal view of the present invention in a stowed position, wherein the forward lip 15 is in contact with the backing surface 14. In this configuration, the device lays flat, and may be easily stored or transported. The device may be carried in a user's pocket, or stored in stack with a plurality of guards prior to use. In use, the forward lip 15 is pulled away from the backing surface, and the inner volume of the guard may be utilized for catching, containing and retaining fluid while attached to the undergarments of a user.

The present invention is an undergarment protection device and sanitary fluid containment pad for use by a male user. The male undergarment guard according to the present invention provides a means to capture bodily fluids and to therefore prevent male undergarments from being soiled by fluids discharged following an erection, post-urination or due to incontinence. The undergarment pad according to present invention has a funnel shape and in the preferred embodiment includes an interior volume or pocket as a means of collection.

The adhesive strips provide a means for attachment of the device to an undergarment of a user. The user removes the film from the adhesive strip and presses the backing surface 14 against the genital region of the undergarment to secure the device thereto. The device may remain in this position until needed, wherein the forward lip 15 may be deployed to collect fluid. In an alternative embodiment, a hygroscopic gel may be utilized within the interior of the device to absorb fluid as it is collected, furthering the ability of the device to protect the user's undergarments from soiling. The material of the device, namely the backing surface, sides and forward lip utilized in the funnel-style construction of the device are preferably a liquid impermeable material to prevent leakage and seepage therethrough.

To this point, the instant invention has been shown and described in what is considered to be the most practical and preferred embodiments. It is recognized, however, that departures may be made there from within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A male undergarment fluid collection device, consisting of:
    a funnel-shaped cup device with a backing surface, a forward lip and sides connecting said backing surface to said forward lip;
    said backing surface upper edge terminating above said forward lip upper edge;
    said backing surface having a shape conforming to an interior surface of a user's undergarment;
    said forward lip adapted to be separated from said backing surface to form an inner volume within said cup device;
    said forward lip also adapted to collapse against said backing surface to provide a flattened device readily storable or transportable;
    an exterior of said backing surface including a T-shaped adhesive bonding; and a hydroscopic gel placed within said inner volume for absorbing fluid.

2. A device as in claim 1, wherein said adhesive bonding is covered by a film prior to use.

3. A device as in claim 1, wherein said backing surface, forward lip and sides are comprised of a liquid impermeable material.

* * * * *